United States Patent
Angros

(10) Patent No.: US 9,176,029 B2
(45) Date of Patent: *Nov. 3, 2015

(54) METHOD OF APPLYING A BIOLOGICAL SPECIMEN TO AN ANALYTIC PLATE

(71) Applicant: Lee H. Angros, Bethany, OK (US)

(72) Inventor: Lee H. Angros, Bethany, OK (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/903,759

(22) Filed: May 28, 2013

(65) Prior Publication Data

US 2013/0260475 A1 Oct. 3, 2013

Related U.S. Application Data

(60) Continuation of application No. 13/485,323, filed on May 31, 2012, now Pat. No. 8,450,116, which is a continuation of application No. 12/624,202, filed on Nov. 23, 2009, now Pat. No. 8,192,994, which is a (Continued)

(51) Int. Cl.
| | |
|---|---|
| *G01N 33/48* | (2006.01) |
| *G01N 1/28* | (2006.01) |
| *G02B 21/34* | (2006.01) |
| *B01L 3/02* | (2006.01) |
| *B01L 3/00* | (2006.01) |

(52) U.S. Cl.
CPC ............ *G01N 1/28* (2013.01); *B01L 3/0293* (2013.01); *G02B 21/34* (2013.01); *B01L 3/0258* (2013.01); *B01L 3/508* (2013.01); *B01L 2300/0822* (2013.01); *Y10T 436/25* (2015.01)

(58) Field of Classification Search
CPC ... B01L 3/5027; B01L 3/5085; B01L 3/5088; B01L 2300/0822; G01N 33/5094; G01N 2035/00138; G01N 2035/00168; G01N 1/28; G01N 1/2813

USPC ................ 422/551, 563; 435/288.3; 436/63
See application file for complete search history.

(56) References Cited

U.S. PATENT DOCUMENTS

| | | | |
|---|---|---|---|
| 3,481,659 | A | 12/1969 | Rosenbert |
| 3,482,898 | A | 12/1969 | Van Den Bosch |
| 3,579,540 | A | 5/1971 | Ohlhausen |
| 3,736,042 | A | 5/1973 | Markovits et al. |
| 3,834,823 | A | 9/1974 | Seregely et al. |

(Continued)

FOREIGN PATENT DOCUMENTS

| | | |
|---|---|---|
| DE | 3830721 A | 3/1990 |
| DE | 19742775 A | 4/1999 |

(Continued)

OTHER PUBLICATIONS

"Introducing Lab-Tek II—The Next Generation" Brochure, Nalge Nunc International, Naperville, IL. Aug. 3, 1996.
Erie Scientific Brochure, Erie Scientific Company, Portsmouth, NH. (Applicant admits that this brochure was published at least one year prior to the filing of the present application submitted herewith).
"ADCELL—The Next Generation in Printed Diagnostic Slides" Brochure, Erie Scientific Company, Portsmouth, NH. (Applicant admits that this brochure was published at least one year prior to the filing of the present application submitted herewith).

(Continued)

*Primary Examiner* — Jill Warden
*Assistant Examiner* — Dwayne K Handy
(74) *Attorney, Agent, or Firm* — Dunlap Codding, P.C.

(57) ABSTRACT

A method of applying a biological specimen to an analytic plate by using an applicator device to apply a coating to the analytic plate and adhering the biological sample to the plate. The coating is substantially transparent, translucent or invisible, and is substantially flush with the surface of the analytic plate. The coating is preferably comprised of a polysiloxane, siloxane, silicone, a silane, a silicon fluid, or a combination thereof and optionally an acid.

17 Claims, 3 Drawing Sheets

Related U.S. Application Data continuation-in-part of application No. 10/989,785, filed on Nov. 16, 2004, now abandoned, which is a continuation of application No. 10/805,777, filed on Mar. 22, 2004, now abandoned, which is a division of application No. 10/225,412, filed on Aug. 20, 2002, now Pat. No. 6,713,304, which is a continuation-in-part of application No. 09/373,468, filed on Aug. 12, 1999, now Pat. No. 6,555,384, which is a continuation-in-part of application No. 09/021,077, filed on Feb. 10, 1999, now Pat. No. 5,948,685, and a continuation-in-part of application No. PCT/US99/02854, filed on Feb. 9, 1999.

(56) References Cited

U.S. PATENT DOCUMENTS

| | | |
|---|---|---|
| 3,883,398 A | 5/1975 | Ono |
| 3,928,142 A | 12/1975 | Smith |
| 4,087,154 A | 5/1978 | Menzel |
| 4,447,140 A | 5/1984 | Campbell |
| 4,481,246 A | 11/1984 | Melisz et al. |
| 4,516,398 A | 5/1985 | Wuchinich |
| 4,521,621 A | 6/1985 | Yanus et al. |
| 4,624,882 A | 11/1986 | Melisz et al. |
| 4,679,914 A | 7/1987 | Rosenberg |
| 4,705,705 A | 11/1987 | Bross |
| 4,790,640 A | 12/1988 | Nason |
| 4,855,201 A | 8/1989 | Badesha et al. |
| 4,867,628 A | 9/1989 | Ammon et al. |
| 4,967,940 A | 11/1990 | Blette et al. |
| 4,974,952 A | 12/1990 | Focht |
| 5,030,551 A | 7/1991 | Herren et al. |
| 5,089,315 A | 2/1992 | Rosenberg |
| 5,111,344 A | 5/1992 | Robinson, Jr. |
| 5,192,503 A | 3/1993 | McGrath et al. |
| 5,348,989 A | 9/1994 | Shiraishi |
| 5,443,791 A | 8/1995 | Cathcart et al. |
| 5,485,527 A | 1/1996 | Bacus et al. |
| 5,571,721 A | 11/1996 | Turner |
| 5,598,295 A | 1/1997 | Olofson |
| 5,683,786 A | 11/1997 | Kavanaugh |
| 5,853,894 A | 12/1998 | Brown |
| 5,948,685 A | 9/1999 | Angros |
| 5,978,072 A | 11/1999 | Nojima |
| 5,989,692 A | 11/1999 | Brown |
| 6,033,738 A | 3/2000 | Teranishi et al. |
| 6,037,168 A | 3/2000 | Brown |
| 6,071,989 A | 6/2000 | Sieber et al. |
| 6,143,496 A | 11/2000 | Brown et al. |
| 6,372,507 B1 | 4/2002 | Angros |
| 6,555,384 B1 | 4/2003 | Angros |
| 6,615,763 B2 | 9/2003 | Edwards |
| 6,713,304 B2 | 3/2004 | Angros |
| 6,759,011 B1 | 7/2004 | Richards et al. |
| 6,818,451 B2 | 11/2004 | Angros |
| 6,855,490 B2 | 2/2005 | Sompuram et al. |
| 6,991,214 B2 | 1/2006 | Richter |
| 7,011,397 B2 | 3/2006 | Miyazawa et al. |
| 8,192,994 B2 | 6/2012 | Angros |
| 8,450,116 B2 | 5/2013 | Angros |
| 2004/0179973 A1 | 9/2004 | Angros |
| 2005/0070026 A1 | 3/2005 | Angros |
| 2007/0187251 A1 | 8/2007 | Ward |

FOREIGN PATENT DOCUMENTS

| | | |
|---|---|---|
| EP | 99905927 | 8/2004 |
| JP | 52008330 A | 1/1977 |
| JP | 62072774 A | 1/1986 |
| JP | 61012773 A | 4/1987 |
| JP | 5062958 | 9/1994 |
| WO | 99/40431 | 8/1999 |

OTHER PUBLICATIONS

"Our Emphasis on Quality Comes From Knowing Our Work Goes Under a Microscope" Brochure, Erie Scientific Company, Portsmouth, NH. (Applicant admits that this brochure was published at least one year prior to the filing of the present application submitted herewith).

"Compatibility of Chamber Slide Components With Various Fixation Reagents", Tech Note, vol. 3, No. 20, Nalge Nunc International, Naperville, IL. (Applicant admits that this brochure was published at least one year prior to the filing of the present application submitted herewith).

"Compatibility of Various Mounting Media on Permanox Slides", Tech Note, Nunc, Inc., Naperville, IL. (Applicant admits that this brochure was published at least one year prior to the filing of the present application submitted herewith).

"Incubation Chambers for Cell Analysis" Brochure, Lab Vision Corp., Fremont, CA. (Applicant admits that this brochure was published at least one year prior to the filing of the present application submitted herewith).

"The Next Generation! Lab-Tek II Chamber Slide System" Brochure, Nalge Nunc international, Naperville, IL. 1998.

"Unelko Corporation Material Safety Data Sheet", Unelko Corporation, Scottsdale, AZ, Jul. 1, 1992.

"United Chemical Technologies Information Brochure", United Chemical Technologies, Inc., 1996.

Sigmacote® Brochure, Sigma Chemical Company, P.O. Box 14508, St. Louis, MO 63178, 3 pages, Apr. 28, 1997.

Isolator™ Hydrophobic Marker from Shandon Lipshaw Catalog, one page, available at least one year prior to Aug. 6, 1999.

Kiyota™ Express-PAP PEN Brochure, Kiyota International, Inc. 1940 E. Devon Ave., Elk Grove Village, IL 60007, two pages, available at least one year prior to Aug. 6, 1999.

ImmEdge™ Pen Brochure, Vector Labs, Inc., vector@vectorlabs.com, two pages, available at least one year prior to Aug. 6, 1999.

Kiyota™ Liquid Blocker [Super PAP PEN], Kiyota International, Inc., 1940 E. Devon Ave., Elk Grove Village, IL 60007, two pages, available at least one year prior to Aug. 20, 2001.

C.D.I.'s Tissue Capture Pen—shows a device used to apply a broad coating to a microscope slide. Available prior to 1998.

Anonymous: "Antibody staining of adult head cryostat sections: (Aug. 29, 1996) PG/Zip lab", Internet Article, [Online] XP002291301, Retrieved from the Internet: URL:http://garrityi.mit.edu/internal/files/protocols/histology/adult%20head20protocols/Mosaic%20Head%2024B10>[retrieved on Aug. 29, 1996].

Leica LMD6000, "Laser microdissection system", Retrieved from the Internet: <URL:http://www.leica-microsystems.com > [retrieved on Aug. 24, 2007].

Technology Start—P.A.L.M. Microlaser, "Technology Start", Retrieved from the Internet < URL:http://palm-microlaser.com > [retrieved on Aug. 24, 2007].

U.S. Appl. No. 10/225,412, Angros, Office Action mailed Feb. 12, 2003, 10 pgs.

U.S. Appl. No. 10/225,412, Angros, Amendment mailed Aug. 12, 2003, 42 pgs.

U.S. Appl. No. 10/225,412, Angros, Declaration of Lee Angros under 37 CFR 1.132 and attachments A-C, mailed Aug. 12, 2003, 11 pgs.

U.S. Appl. No. 10/225,412, Angros, Notice of Allowability, mailed Nov. 10, 2003, 7 pgs.

U.S. Appl. No. 09/373,468, Angros, Office Action mailed Sep. 19, 2001, 7 pgs.

U.S. Appl. No. 09/373,468, Angros, Amendment mailed Dec. 18, 2001, 15 pgs.

U.S. Appl. No. 09/373,468, Angros, Office Action mailed Jan. 17, 2002, 6 pgs.

U.S. Appl. No. 09/373,468, Angros, Response to Rejection mailed Mar. 15, 2002, 4 pgs.

U.S. Appl. No. 09/373,468, Angros, Notice of Allowance (NOA) mailed Mar. 1, 2002, 1 pg.

METHOD OF APPLYING A BIOLOGICAL SPECIMEN TO AN ANALYTIC PLATE

CROSS-REFERENCE TO RELATED APPLICATIONS

The present application is a continuation of U.S. Ser. No. 13/485,323, filed May 31, 2012, now U.S. Pat. No. 8,450,116, which is a continuation of U.S. Ser. No. 12/624,202, filed Nov. 23, 2009, now U.S. Pat. No. 8,192,994, which is a continuation-in-part of U.S. Ser. No. 10/989,785, filed Nov. 16, 2004, now abandoned, which is a continuation of U.S. Ser. No. 10/805,777, filed Mar. 22, 2004, now abandoned, which is a divisional application of U.S. Ser. No. 10/225,412, filed Aug. 20, 2002, now U.S. Pat. No. 6,713,304, which is a continuation-in-part of U.S. Ser. No. 09/373,468, filed Aug. 12, 1999, now U.S. Pat. No. 6,555,384, which is a continuation-in-part of U.S. Ser. No. 09/021,077, filed Feb. 10, 1998, now U.S. Pat. No. 5,948,685, and which is also a continuation-in-part of International Application No. PCT/US99/02854 filed Feb. 9, 1999. Each of the patents or applications listed above is hereby expressly incorporated by reference herein in its entirety.

BACKGROUND

The present invention relates generally to the field of applying biological specimens analytic plates.

Standard microscope slides and diagnostic plates are thin, typically rectangular, sheets of glass, ceramic, or plastic. In use, a sample comprising an aqueous or non-aqueous liquid, liquid reagent, biological fluid and/or biological tissue section(s) is placed upon a portion of the slide or diagnostic glass plate. Before analysis, the sample on the slide or plate may be dried, placed in a fixative, or remain fresh prior to treatment for enhanced visualization by light, electron, or fluorescent microscopy, and/or including gross analysis with the human eye. The sample may be analyzed in its natural state or may need treatment with one or more liquid dyes to enhance visualization. Further treatment with molecular biological techniques may include, for example, treatment by monoclonal, polyclonal antibodies, in-situ hybridization by molecular probes, and/or their liquid detection reagents. During routine analysis or manipulation of a slide or plate, the sample or liquid reagent may spill from the slide, run or migrate onto other portions of the slide, and/or "wick off" if the slide touches another object, thus resulting in a loss of all or part of the liquid sample or reagent. It is desirous to avoid such inadvertent or undesired mixing or contamination of different samples or liquid reagents.

It is therefore beneficial for the slide or diagnostic plate to have means to confine the sample or liquid used in treating the sample to a specific area on the slide or plate. This has been accomplished previously by creating a slide or plate having one or more depressions, or "wells" therein. Alternatively, a physical barrier or hydrophobic material may be applied to the slide surface in a bordered pattern to confine the liquid applied to the plate within the area surrounded by the border. Such borders may comprise a coating of Teflon, paint, wax, paraffin, epoxy resin, or other resinous material. Each of these materials results in a border having a thickness resulting in a raised border extending a distance above the surface of the glass, for example, a Teflon layer is generally from about 0.001 to about 0.0025 inches high. These raised areas are generally opaque and the end result is a loss of the transparent nature of the slide where the border is applied. In spite of the fact that these raised borders may be somewhat effective in confining the liquid, there continues to be a need for a slide or plate which achieves confinement of the liquid upon a slide while maintaining transparency of the glass or plate. It is the object of the present invention to provide such a slide.

SUMMARY OF THE INVENTION

The present invention contemplates an analytic plate such as a microscope slide or a diagnostic plate having a containment border for inhibiting migration of liquids or liquid samples thereon, wherein the border is substantially transparent and is substantially flush with the surface of the slide or plate and which covers only a portion of the surface of the slide or plate, and a method of making such a plate or slide.

BRIEF DESCRIPTION OF THE DRAWINGS

FIG. 7 is a perspective view of a pen used in accordance with the present invention.

DETAILED DESCRIPTION OF THE INVENTION

The present invention contemplates an analytic plate such as a microscope slide or a diagnostic plate having a containment border for inhibiting migration of liquids or liquid samples thereon, wherein the border is substantially transparent and is substantially flush with the surface of the slide or plate and which covers only a portion of the surface of the slide or plate.

Where used herein, the term "analytic plate" refers to those types of plates such as microscope slides and diagnostic plates which are used, for example, in microscopic analysis or diagnostic analysis or comparison of samples. Analytic plates are generally comprised of glass or plastic (translucent, transparent, or opaque) but may also comprise ceramic materials. The analytic plates contemplated herein can have any shape suitable for use in analytic devices wherein the analytic plate can hold or contain a liquid or sample for analysis. When used herein, the terms, "plate" and "slide" are intended to be interchangeable.

Figure 1A:
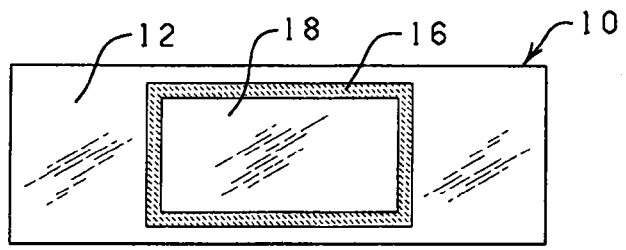
FIG. 1A is a plan view of a microscope slide constructed in accordance with the present invention.
Figure 1B:
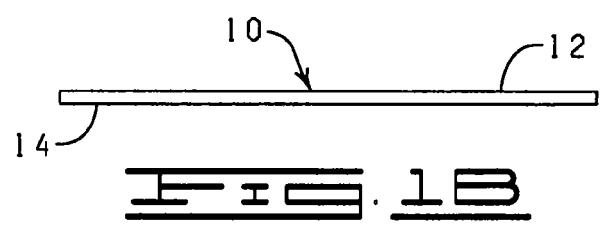
FIG. 1B is a side view of the slide of FIG. 1A.

Referring now to FIGS. 1A and 1B, a glass microscope slide having the general reference numeral 10 is shown. The slide 10 has a conventional length, width and thickness as is well known to one of ordinary skill in the art. The slide 10 has an upper surface 12 and a lower surface 14. Disposed upon a portion of the upper surface 12 is a liquid containment border 16 which in the version of FIG. 1A has a rectangular shape. Where used herein the term "liquid containment border" or "containment border" refers to a transparent border which prevents passage of an aqueous or non-aqueous liquid thereacross. The containment border 16 surrounds a containment area 18 of the upper surface 12 of the slide 10. The containment border 16 forms a liquid barrier about the containment area 18. When a liquid or liquid sample (not shown) is placed upon the containment area 18 of the slide 10 for analysis, the containment border 16 prevents the spreading, leakage or migration of the liquid or liquid sample from the containment area 18, thus causing the sample to be retained in a discrete and confined location upon the slide 10. Where used herein, the term liquid or liquid sample is intended to refer to a liquid material, or a liquid biological sample (e.g., blood, urine, plasma, or cerebrospinal fluid) which is desired to be localized on the slide.

The coating material which is used to form the containment border 16 comprises a material which when applied to the slide 10 is preferably transparent or clear although it may have a color to indicate its position on the slide or have printed, by one of ordinary skill in the art, on the lower surface 14 and/or upper surface 12 of the slide 10 information (lines or numbers or symbols) indicating the position of the containment border 16 on the upper surface 12. The containment border 16 forms a molecular layer when dry and therefore is substantially flush (level) with the upper surface 12 of the slide 10. The containment border 16 is therefore not raised above the upper surface 12 to a degree that is visible to the naked eye. In fact, the containment border 16 preferably has a thickness of less than 0.0001 inch and more preferably less than 0.00001 inch. After the coating material is applied to the slide 10 thereby forming the containment border 16, the slide 10 is dried. The containment border 16 may be transparent or translucent after application, wherein it may be desired to buff or treat the slide 10 chemically (e.g., by xylene, alcohol, or acetone, or other commonly used laboratory solvents) such that the containment border 16 is preferably rendered clear (transparent) and invisible whereby the containment border 16 leaves the refractive index of the slide 10 unaltered when viewed through a microscope.

In a preferred embodiment the coating material which forms the containment border 16 is a composition comprising a liquid repellant compound dissolved in a volatile solvent. In a particularly preferred version, the composition comprises an alkyl polysiloxane and a mineral acid mixed with a solvent in a manner well known in the art. Such a mixture is described in U.S. Pat. No. 3,579,540, the specification of which is hereby incorporated herein by reference in its entirety. Other polysiloxanes, siloxanes, silanes, silicones, silicon fluids, and combinations thereof which can permanently or at least substantially permanently bond to a glass surface and function in accordance with the present invention are also contemplated and are well known in the art, and are available commercially for use herein. Although a polysiloxane acid mixture is particularly preferred, it will be understood by one of ordinary skill in the art that any material which can adhere to the surface of at least one of a glass, plastic or ceramic slide or plate and which forms a substantially non-raised molecular layer as described and claimed herein and is suitable for use in the present invention.

It is generally necessary to apply a coating material composition comprising at least 1% by weight of the polysiloxane, siloxane, silane, silicone, silicon fluid or combinations thereof to provide a containment border 16 having sufficient liquid repellancy properties for the slide 10 with the containment border 16 thereon to function as contemplated in the present invention herein. More preferably the composition of the coating material comprises at least 2.5%, 5%, 10%, 15%, 20% or 25% of the polysiloxane, the siloxane, the silane, the silicone, the silicon fluid, or combinations thereof.

The coating material can be applied to the slide 10 in any manner known in the art for applying a liquid to a surface, for example, by brushing, wiping, by using a stamping device, by spraying or by application from a device (such as a pen or pen-like device) filled with the coating material to be applied to the slides or plates (described in more detail below).

In an alternative method of application of the coating material for the containment border 16, the slide 10 may be provided with a removable raised layer of a material such as a silicone rubber which is applied as a raised strip on a portion of the upper surface 12 of the slide 10 (not shown). Prior to the application of the liquid or liquid sample for treatment, the raised silicone strip is peeled away from the upper surface 12 of the slide 10, leaving a residual coating comprising the containment border 16 in accordance with the present invention. After the raised silicone rubber strip has been peeled away leaving the containment border 16, the slide 10 can be used in accordance with the present invention.

It is another distinctive characteristic of the present invention that, in a preferred embodiment, after the coating material is applied to the slide 10 to form the containment border 16 and the coating material has dried thereon, the containment border 16 is highly resistant to abrasion and to chemical removal and physical removal by washing, scrubbing, wiping, placement in organic solvents, inorganic solvents, and aqueous solvents. The slide 10 can therefore be used repeatedly without the containment border 16 losing its repellant properties.

The containment border 16 of the present slide 10 is further distinguished from prior art slides which have Teflon borders or other physical barriers because the surface of such prior art slides must be treated before the Teflon coating can adhere to the slide (e.g., using an adhesive) thus causing solvents to dissolve the adhesive and the subsequent loss of the border's efficiency due to peeling and/or loss of the liquid confinement integrity of the border. The borders of slides using coatings of Teflon, epoxy, or paint are generally opaque and are raised above the surface of the slide, unlike the borders on the slides of the present invention. In the present invention, there is no intervening layer (e.g., an adhesive) between the glass and the coating comprising the containment border 16. Further, borders of such prior art slides also suffer from non-specific binding of reagents along their raised edges thereby causing interference with the specimen.

For example, interference may occur when the reagents used in processing biological samples adhere, are drawn to, or react with these raised borders causing undesirable background staining around the specimen. Additionally, these raised borders cause "pooling" of reagents in the "well" formed by the raised border, making rinsing of reagents more difficult than the non-raised borders of the present invention.

The present invention also enables the user to coverslip the slides with known manual and automated coverslipping methods without the need to add excess mountant into the space within the raised wells to fill the gaps of "dead air" space resulting from the raised borders. These "dead air" spaces, if not filled with mountant, would have bubbles present under the coverslip, which is undesirable. The substantially non-raised borders of the present invention do not interfere with the placement of the coverslip on the slide nor do they necessitate the addition of mountant beyond the normal amount of mountant necessary for a normal untreated slide to be coverslipped.

Another advantage of the slide of the present invention relates to the transparent nature of the border. Recent developments in image analysis has advanced specimen scanning to offer a reproducible analysis of specimens on a slide. These instruments automatically or semi-automatically scan the slide to find the specimen and measure variables. The need to maintain the transparent nature of the slide is critical. The camera scans the slides and picks up anything that alters the light path, therefore, it is important that the only object on the slide which alters the light passing through the camera is the specimen itself, not an opaque border that would typically block the entire light path.

Figure 2A:
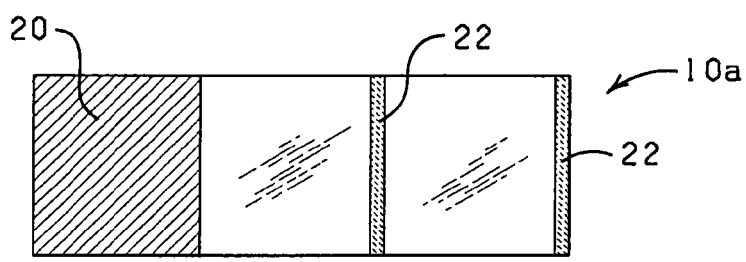
FIG. 2A is a plan view of another version of a microscope slide constructed in accordance with the present invention.
Figure 2B:
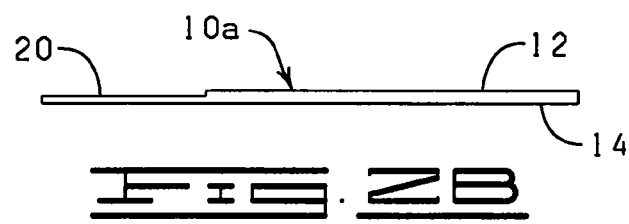
FIG. 2B is a side view of the slide of FIG. 2A.

Although the microscope slide of the present invention may consist solely of a slide 10 with the containment border 16 thereon, in some embodiments the slide may further have a distinct marking surface thereon for writing upon or for attaching a label thereto. FIGS. 2A and 2B show such a slide, designated therein by the general reference numeral 10a. The slide 10a has a marking surface 20 which is a "frosted" portion of the slide 10a (i.e., a portion of the slide 10a which has been etched off or abraded). In an alternative version of such a slide, the marking surface 20 may be an opaque epoxy or painted coating. Other means of forming a marking surface will be apparent to one of ordinary skill in the art. FIG. 2A further shows an alternative version of the invention wherein the containment border, designated by the general reference numeral 22 comprises a pair of strips extending from one edge of the slide to another, rather than forming a box pattern as shown in slide 10a.

Figure 3:
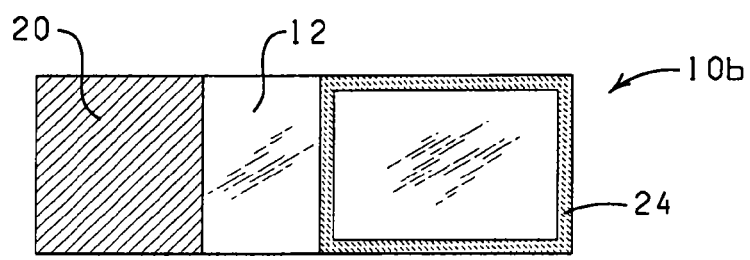
FIG. 3 is a plan view of another version of a microscope slide constructed in accordance with the present invention.
Figure 4:
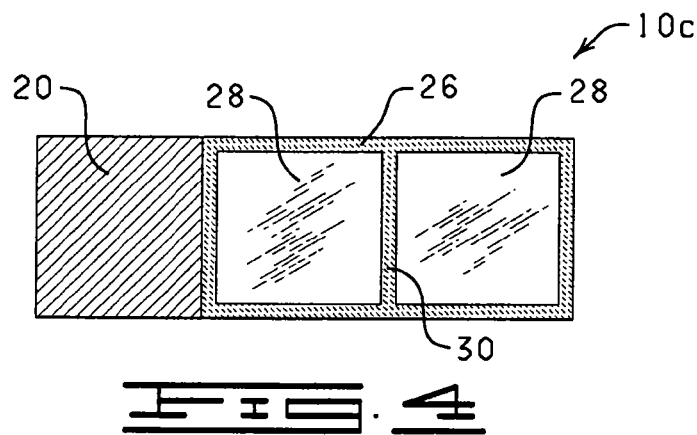
FIG. 4 is a plan view of another version of a microscope slide constructed in accordance with the present invention.

FIG. 3 shows a slide 10b which is essentially the same as slide 10a except the containment border is a border 24 which forms an entire "box" on the surface 12 of the slide 10b. FIG. 4 shows an alternative embodiment of the invention, a slide 10c having a containment border 26 which comprises a pair of separate containment areas 28. The separate containment areas 28 can therefore contain separate samples which are prevented from mixing by the portion 30 of the containment border 26 which separates the two containment areas 28. Although not specifically shown in the figure, the slide 10c may be constructed to comprise a plurality of separate containment areas 28 greater than two for holding a plurality of samples, as will be understood by a person of ordinary skill in the art.

Figure 5:
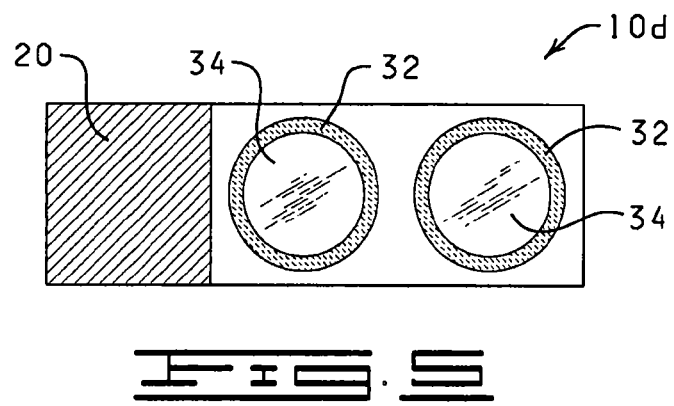
FIG. 5 is a plan view of another version of a microscope slide constructed in accordance with the present invention.
Figure 6:
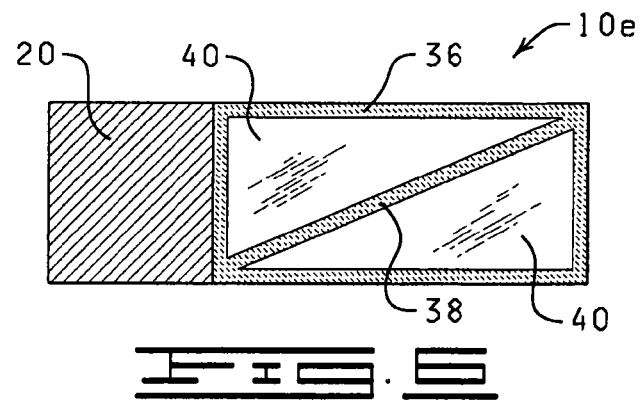
FIG. 6 is a plan view of another version of a microscope slide constructed in accordance with the present invention.
Figure 3:
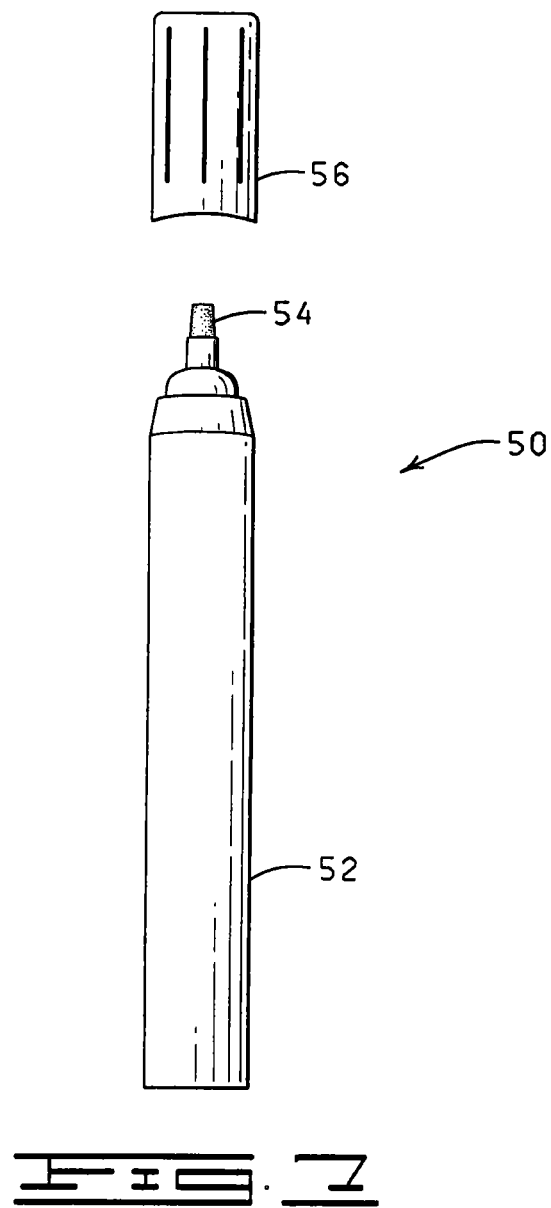

FIG. 5 shows a slide 10d having a pair of circular containment borders 32 which surround containment areas 34. Alternative versions of slide 10d may have only a single circular containment border 32, or may have a plurality of circular containment borders 32. FIG. 6 shows a slide 10e comprising a containment border 36 having a diagonal border 38 extending thereacross forming a pair of triangle shaped containment areas 40. Alternative versions of the slide 10e may have only a single triangle shaped containment area 40, or may have a plurality of areas 40. Further, it will be understood by a person of ordinary skill in the art that the shapes of the containment areas are not limited only to those shown in the figures herein. The containment areas may have other shapes, such as ovals, stars, ellipses, pentagons, hexagons, trapezoids, or even non-geometric or fanciful shapes. Further, a single slide may have more than one particular shape of containment border disposed thereon, for example, a circle and a box or a pair of circles and a pair of boxes.

As is evident from the above, each slide contemplated herein has only a portion of its surface having a coating made from the coating material, with the specific purpose for retaining a biological sample upon a discrete and predetermined portion of the slide.

In an alternative embodiment of the invention, one or more of the microscope slides or plates contemplated herein may be supplied as a kit along with other components used in microscopic analysis of samples. Said other components may comprise stains and reagents commonly used by those of ordinary skill, including but not limited to, stains, dyes, molecular biological reagents including monoclonal and polyclonal antibodies, and molecular probes and their detection reagents, and other aqueous and non-aqueous processing reagents. Examples of aqueous and non-aqueous processing reagents include xylene, toluene, acetone, and other organic and inorganic solvents, and alcohols, biological buffers, and aqueous reagents for use with antibodies, and molecular probes and their detection reagents.

As noted above, the containment border may be applied via a pen, or pen-like device, an example of which is shown in FIG. 7. The pen is designated by reference number 50 and comprises a body 52 having a reservoir therein (not shown) which contains a quantity of the liquid composition comprising a coating material described elsewhere herein (e.g., polysiloxane). The pen 50 further comprises an applicator end 54, and a cap 56 for inhibiting evaporation of the coating material or drying of the tip 54. The pen 50 or cap 56 may comprise means for clipping, e.g., to a pocket. The applicator end may be a brush, a swab, a rubber tip, or any other device known to one of ordinary skill in the art of applicator pens.

As contemplated herein, a user can use the pen 50 to custom make his own "bordered slides" having a containment border as described herein. The border applied in such a manner is resistant to removal by organic solvents such as xylene, as described above. In use, the user applies a layer of the coating material, e.g., polysiloxane, to a slide, allows it to dry, then applies the aqueous or non-aqueous liquid or histological material, or other biological sample, and carries out various processing steps known in the art for analyzing the specimen (e.g., treating with stains and organic solvents). Alternatively, the sample may be applied to the slide before the containment border is applied to the slide, e.g., a list of any tissue sample or any other biological sample that requires air drying before processing. Treatment with organic solvents used in the processing steps has substantially no effect on the durable containment border as claimed herein. The pen applicator of the present invention differs from other pen applicators known in the art (e.g., PAP Pen) because such prior art pens are used only to apply a greasy or oily layer to the slide which is neither resistant to abrasion or rubbing nor resistant to organic solvents, i.e., the layer can be physically wiped or worn off and is not resistant to most organic solvents such as xylene. The containment borders provided by using the pen 50 described herein are resistant to abrasion or to removal by organic solvents. Further, in an especially preferred version of the present invention, the coating material used in the pen 50 does not contain or comprise an oil.

The examples described herein are not intended to limit the scope of the invention. Changes may be made in the construction and the operation of the various components, elements and assemblies described herein or in the steps or the sequence of steps of the methods described herein without departing from the scope of the invention as defined in the following claims.

What is claimed is:

1. A method of applying a biological sample to an analytic plate, comprising:

applying a fluid composition to a surface of the analytic plate with an applicator to form a containment border extending from one edge of the analytic plate to an opposing edge thereof, the applicator being a pen or pen-like device having a body with a reservoir and an applicator end with a tip extending from the body, the fluid composition being positioned in the reservoir and comprising a polysiloxane, a siloxane, a silane, a silicone, a silicon fluid, or a combination thereof, wherein the fluid composition is applied to the surface of the analytic plate by appressing the tip of the applicator end to the surface of the analytic plate to cause the fluid composition to flow from the reservoir of the body, through the tip, and onto the surface of the analytic plate to form the containment border in a way that the containment border has a thickness of less than 0.0001 inches after drying; and applying the biological sample to the surface of analytic plate after the containment border has been applied to the analytic plate.

2. The method of claim 1, wherein the containment border is in the form of at least one strip.

3. The method of claim 2 wherein the strip has a thickness of 0.00001 inches or less.

4. The method of claim 2, wherein the analytic plate has a length and a width, and wherein the strip is formed to extend across the width of the analytic plate.

5. The method of claim 4, wherein the strip is formed in a spaced apart, parallel relationship to at least one edge of the analytic plate.

6. The method of claim 5, wherein the biological sample is applied to the analytic plate between the strip and the edge of the analytic plate.

7. The method of claim 2, wherein the strip is a first strip, and wherein the method further comprises the step of applying the fluid composition to the surface of the analytic plate with the applicator to form a second strip extending from one edge of the analytic plate to the opposing edge thereof in a spaced apart relationship to the first strip.

8. The method of claim 7 wherein each of the first strip and the second strip has a thickness of 0.00001 inches or less.

9. The method of claim 7, wherein the biological sample is applied to the surface of the analytic plate between the first strip and the second strip.

10. The method of claim 1, wherein the containment border has a thickness of 0.00001 inches or less.

11. The method of claim 1, wherein the analytic plate is glass.

12. The method of claim 1, wherein the containment border is colorless.

13. The method of claim 1, wherein the containment border is transparent.

14. The method of claim 1, wherein the containment border is translucent.

15. The method of claim 1, wherein the containment border is invisible.

16. The method of claim 1, wherein the containment border is transparent, translucent, or invisible and is resistant to removal and abrasion.

17. The method of claim 1, wherein the analytic plate is glass and wherein the refractive index of the analytic plate is substantially unaltered by the containment border when viewed through a microscope.

* * * * *